(12) United States Patent
Douk et al.

(10) Patent No.: US 7,371,249 B2
(45) Date of Patent: May 13, 2008

(54) TEMPORARY INTRALUMINAL FILTER GUIDEWIRE AND METHODS OF USE

(75) Inventors: Nareak Douk, Lowell, MA (US); Nasser Rafiee, Andover, MA (US); David S. Brin, Danvers, MA (US); Peter G. Strickler, Tewksbury, MA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 456 days.

(21) Appl. No.: 11/053,368

(22) Filed: Feb. 8, 2005

(65) Prior Publication Data

US 2005/0149113 A1  Jul. 7, 2005

Related U.S. Application Data

(62) Division of application No. 09/824,832, filed on Apr. 3, 2001, now Pat. No. 6,866,677.

(51) Int. Cl.
*A61M 29/00* (2006.01)

(52) U.S. Cl. .................................................. 606/200

(58) Field of Classification Search ................ 606/113, 606/114, 127, 159, 200, 194, 198; 623/1.11, 623/1.13, 1.2
See application file for complete search history.

(56) References Cited

U.S. PATENT DOCUMENTS

| | | |
|---|---|---|
| 3,996,938 A | 12/1976 | Clark, III |
| 4,577,631 A | 3/1986 | Kreamer |
| 4,650,466 A | 3/1987 | Luther |
| 4,875,489 A | 10/1989 | Messner et al. |
| 4,926,858 A | 5/1990 | Gifford et al. |
| 5,034,001 A | 7/1991 | Garrison et al. |
| 5,263,963 A | 11/1993 | Garrison et al. |
| 5,265,622 A | 11/1993 | Barbere |
| 5,329,942 A | 7/1994 | Gunther et al. |
| 5,330,482 A | 7/1994 | Gibbs et al. |
| 5,376,094 A | 12/1994 | Kline |
| 5,483,022 A | 1/1996 | Mar |
| 5,569,184 A | 10/1996 | Chum et al. |
| 5,628,787 A | 5/1997 | Mayer |

(Continued)

FOREIGN PATENT DOCUMENTS

EP 0321912 6/1989

(Continued)

OTHER PUBLICATIONS

Hodgson, D.E. et al. "Augmented Properties of NiTi Wire by 'Filling' with Selected Metals" SMST-97: Proceedings of the Second International Conference on Shape Memory and Superelastic Technologies, pp. 461-465, 1997.

*Primary Examiner*—Kevin T. Truong
(74) *Attorney, Agent, or Firm*—James F. Crittenden

(57) ABSTRACT

The present invention is a temporary intraluminal filter guidewire for use during interventional procedures, such as angioplasty or stent deployment. A braided filter is mounted near the distal end of a steerable guidewire, which guides a therapeutic catheter. An actuator rod slides over the guidewire and is removably connected to the filter. The rod controls relative displacement of the filter ends, causing transformation of the filter between a deployed configuration and a collapsed configuration. Wire having enhanced radiopacity is included in the filter to provide visualization under fluoroscopy.

12 Claims, 10 Drawing Sheets

U.S. PATENT DOCUMENTS

| | | |
|---|---|---|
| 5,630,840 A | 5/1997 | Mayer |
| 5,679,470 A | 10/1997 | Mayer |
| 5,725,570 A | 3/1998 | Heath |
| 5,765,418 A | 6/1998 | Rosenberg |
| 5,800,511 A | 9/1998 | Mayer |
| 5,814,064 A | 9/1998 | Daniel et al. |
| 5,824,056 A | 10/1998 | Rosenberg |
| 5,824,077 A | 10/1998 | Mayer |
| 5,910,154 A | 6/1999 | Tsugita et al. |
| 5,911,734 A | 6/1999 | Tsugita et al. |
| 5,935,139 A | 8/1999 | Bates |
| 5,972,019 A | 10/1999 | Engelson et al. |
| 6,001,118 A | 12/1999 | Daniel et al. |
| 6,017,362 A | 1/2000 | Lau |
| 6,027,520 A | 2/2000 | Tsugita et al. |
| 6,042,598 A | 3/2000 | Tsugita et al. |
| 6,053,932 A | 4/2000 | Daniel et al. |
| 6,059,814 A | 5/2000 | Ladd |
| 6,066,158 A | 5/2000 | Engelson et al. |
| 6,096,053 A | 8/2000 | Bates |
| 6,123,715 A | 9/2000 | Amplatz |
| 6,152,946 A | 11/2000 | Broome et al. |
| 6,165,200 A | 12/2000 | Tsugita et al. |
| 6,171,327 B1 | 1/2001 | Daniel et al. |
| 6,179,859 B1 | 1/2001 | Bates et al. |
| 6,187,025 B1 * | 2/2001 | Machek .................. 606/200 |
| 2003/0023227 A1 | 1/2003 | Zadno-Azzi et al. |

FOREIGN PATENT DOCUMENTS

| | | |
|---|---|---|
| EP | 0771549 | 5/1997 |
| WO | WO 96/01591 | 1/1996 |
| WO | WO 98/47447 | 10/1998 |
| WO | WO 99/22673 | 5/1999 |
| WO | WO 99/23976 | 5/1999 |
| WO | WO 99/44510 | 6/1999 |
| WO | WO 01/16705 | 3/2000 |
| WO | WO 00/67664 | 11/2000 |
| WO | WO 00/67667 | 11/2000 |
| WO | WO 00/67671 | 11/2000 |
| WO | WO 01/08595 | 2/2001 |
| WO | WO 01/45592 | 6/2001 |

* cited by examiner

TEMPORARY INTRALUMINAL FILTER GUIDEWIRE AND METHODS OF USE

This application is a Divisional of prior U.S. patent application Ser. No. 09/824,832, filed Apr. 3, 2001 now U.S. Pat. No. 6,866,677.

FIELD OF THE INVENTION

The present invention relates generally to intraluminal devices for capturing particulate in the vessels of a patient. More particularly, the invention relates to a filter for capturing emboli in a blood vessel during an interventional vascular procedure and then removing the captured emboli from the patient after completion of the procedure. Furthermore, the invention concerns a filter mounted on a guidewire that can also be used to direct an interventional catheter to a treatment site within a patient.

BACKGROUND OF THE INVENTION

A variety of treatments exists for dilating or removing atherosclerotic plaque in blood vessels. The use of an angioplasty balloon catheter is common in the art as a minimally invasive treatment to enlarge a stenotic or diseased blood vessel. When applied to the vessels of the heart, this treatment is known as percutaneous transluminal coronary angioplasty, or PTCA. To provide radial support to the treated vessel in order to prolong the positive effects of PTCA, a stent may be implanted in conjunction with the procedure.

Thrombectomy is a minimally invasive technique for removal of an entire thrombosis or a sufficient portion of the thrombosis to enlarge the stenotic or diseased blood vessel and may be accomplished instead of a PTCA procedure. Atherectomy is another well known minimally invasive procedure that mechanically cuts or abrades a stenosis within the diseased portion of the vessel. Alternatively, ablation therapies use laser or RF signals to superheat or vaporize the thrombus within the vessel. Emboli loosened during such procedures may be removed from the patient through the catheter.

During each of these procedures, there is a risk that emboli dislodged by the procedure will migrate through the circulatory system and cause infarction or strokes. Thus, practitioners have approached prevention of escaped emboli through use of occlusion devices, filters, lysing and aspiration techniques. For example, it is known to remove the embolic material by suction through an aspiration lumen in the treatment catheter or by capturing emboli in a filter or occlusion device positioned distal of the treatment area.

Prior art temporary filters or occlusion devices are associated with either a catheter or guidewire and are positioned downstream of the area to be treated. One prior art filter arrangement includes a dilatation balloon and a filter mounted on the same catheter. The filter is located distal to the dilatation balloon and consists of a filter material secured to resilient ribs. A filter balloon is located between the catheter exterior and the ribs. Inflation of the filter balloon extends the ribs outward across the vessel to form a trap for fragments loosened by the dilatation balloon. When the filter balloon is deflated, the resilient ribs retract against the catheter to retain the fragments during withdrawal of the catheter.

Another prior art device includes a filter mounted on the distal portion of a hollow guidewire or tube. A moveable core wire is used to open and close the filter. The filter is secured at the proximal end to the tube and at the distal end to the core wire. Pulling on the core wire while pushing on the tube draws the ends of the filter toward each other, causing the filter framework between the ends to expand outward into contact with the vessel wall. Filter mesh material is mounted to the filter framework. To collapse the filter, the procedure is reversed; pulling on the tube while pushing on the core wire to draw the filter ends apart.

Another prior art device has a filter made from a shape memory material. The device is deployed by moving the proximal end of the filter towards the distal end. It is collapsed and withdrawn by sliding a sheath over the filter and then removing the sheath and filter together.

A further prior art filter device discloses a compressible polymeric foam filter mounted on a shaft that is inserted over a guidewire. The filter is inserted collapsed within a housing which is removed to deploy the filter once in position. The filter is retracted by inserting a large bore catheter over the shaft and the filter, and then removing the shaft, filter and catheter together.

Another prior art filter arrangement has a filter comprised of a distal filter material secured to a proximal framework. This filter is deployed in an umbrella manner with a proximal member sliding along the shaft distally to open the filter and proximally to retract the filter. A large separate filter sheath can be slid onto the shaft and the filter is withdrawn into the sheath for removal from the patient.

Other known prior art filters are secured to the distal end of a guidewire with a tubular shaft. Stoppers are placed on the guidewire proximal and distal of the filter, allowing the filter to move axially independently of the guidewire. A sheath is used to deploy and compress the filter.

However, the guidewire-based filter devices do not have the handling characteristics expected of steerable guidewires. Abrupt transitions in stiffness in the area of the filter can limit the ability of the guidewire to negotiate tortuous vascular anatomy. Such device limitations can restrict the number of patients receiving the benefits of filtration during interventional vascular procedures. Filter guidewires that use a moveable core wire to actuate the filter also have diminished performance characteristics.

Another problem associated with prior art filter guidewires is the requirement for a sheath to envelop and collapse the filter before and after the treatment is performed. Sheaths that encase the filter often require large bores, with attendant bulky handling. It is time-consuming and cumbersome to exchange the sheath for the treatment catheter and to reverse this exchange step at the end of the procedure.

Another problem associated with self-expanding temporary filters is visualization of the filter under fluoroscopy. Filter braiding materials having good mechanical properties are not also very radiopaque to X-rays typically used during clinical procedures. Solutions to this problem typically require the addition of radiopaque material to the braiding wires, which often diminishes their shape-memory or elastic properties, or both.

With the above in mind, it is an object of the present invention to provide a filter guidewire with improved handling characteristics.

Another object of the present invention is to provide a filter guidewire that does not require an enveloping sheath to collapse the filter for insertion or withdrawal.

Another object of the invention is to provide a radiopaque temporary filter with undiminished physical performance.

SUMMARY OF THE INVENTION

The present invention is a temporary filter guidewire for use in intraluminal procedures. The device includes a filter assembly mounted adjacent the distal end of a guidewire used in the procedure. The filter is a tubular assembly that expands in the middle region when the ends are drawn toward each other. The filter assembly includes an expandable frame with a distal portion acting as the emboli filter. The emboli filter is sized sufficiently to expand and cover the lumen of the vessel distal to the intended treatment area.

In one embodiment of the invention, the guidewire includes a moveable core wire having a tapered distal end to which the distal end of the filter is attached. The proximal end of the filter is attached to the distal end of the guidewire tubular shaft. The guidewire shaft includes a stiff, elongate proximal portion for steering and transmitting axial force, and a relatively flexible distal portion for negotiating tortuous vascular anatomy. A transition sleeve is fixed to the core wire and fits slidingly inside the distal end of the tubular shaft. The sleeve extends distal to the shaft, providing a smooth transition in stiffness where an abrupt change would otherwise occur. The combination of tapered core wire, flexible distal shaft region and transition sleeve results in a filter guidewire with handling characteristics that are comparable to standard steerable guidewires.

Another embodiment of the invention is built around a standard-type steerable guidewire, which includes an elongate shaft having a distal region surrounded by a flexible tubular element, such as a coiled spring. Both the proximal and distal ends of a self-expanding tubular filter assembly are slidably mounted adjacent the distal end of the guidewire, with a stop element fixed to the guidewire between the filter ends to limit axial movement thereof. Mounted to the proximal end of the filter is a sliding actuator, which is selectively engageable with a hollow rod slidably disposed over the guidewire. Proximally directed force can be applied to the filter proximal end by pulling the combination of the rod and the actuator while pushing the guidewire distally. A first degree of such proximally directed force will collapse the filter by separating the filter proximal end from the filter distal end, which is restrained against proximal movement by the stop element. A second, higher degree of proximally directed force will disengage the rod from the actuator, permitting the rod to be withdrawn from the patient and allowing the filter to self-expand.

In a third embodiment of the invention, a tubular filter assembly is mounted adjacent the distal end of a standard-type steerable guidewire, which is described above. The distal end of the filter is slidably mounted to the guidewire, and the proximal end is fixed thereto. An actuator mechanism includes a link element slidably extending through the proximal end of the filter to provide a mechanical connection between the distal end of the filter and a proximal tubular control element. In this embodiment of the invention, the actuator mechanism reverses the push-pull action used for transforming the filter between collapsed and deployed configurations in the prior art and in the first and second embodiments of the invention. In this embodiment, pulling on the guidewire and pushing on the tubular control element causes the filter to be collapsed, rather than deployed.

In the third embodiment of the invention, the actuator is slidably mounted over the guidewire and can be either an elongate hollow rod or a short ring. In the embodiment having the elongate rod, the rod can be manipulated directly from the proximal end of the device. In the embodiment having a short ring, the ring is operable by a removable hollow rod or tube, which may comprise a therapeutic catheter.

To provide a temporary filter with enhanced radiopacity, but with undiminished physical performance, radiopaque material is added to one or more braiding wires, in the centers thereof, where the effect on physical properties of the wires is minimized.

DESCRIPTION OF THE PREFERRED EMBODIMENTS

Figure 1:
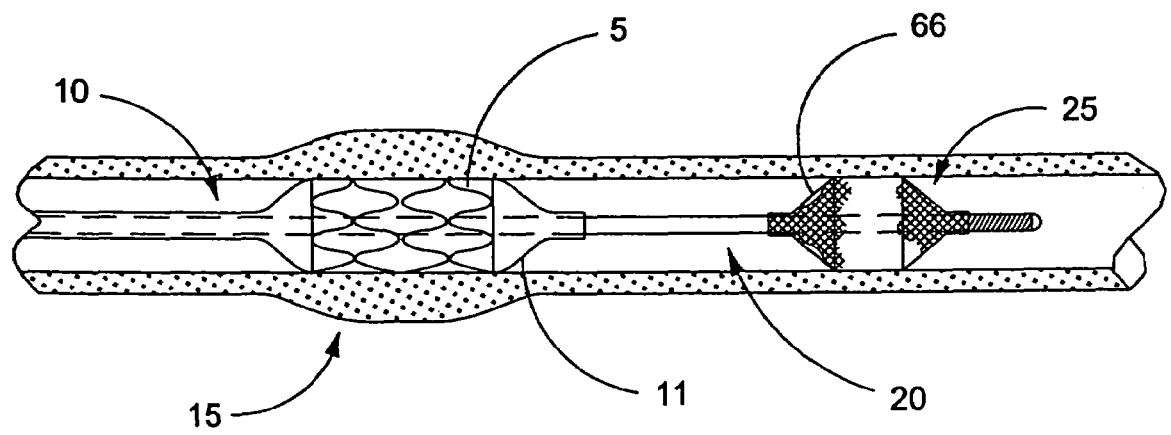
FIG. 1 is an illustration of a filter system in accordance with the invention deployed within a blood vessel.
Figure 2:
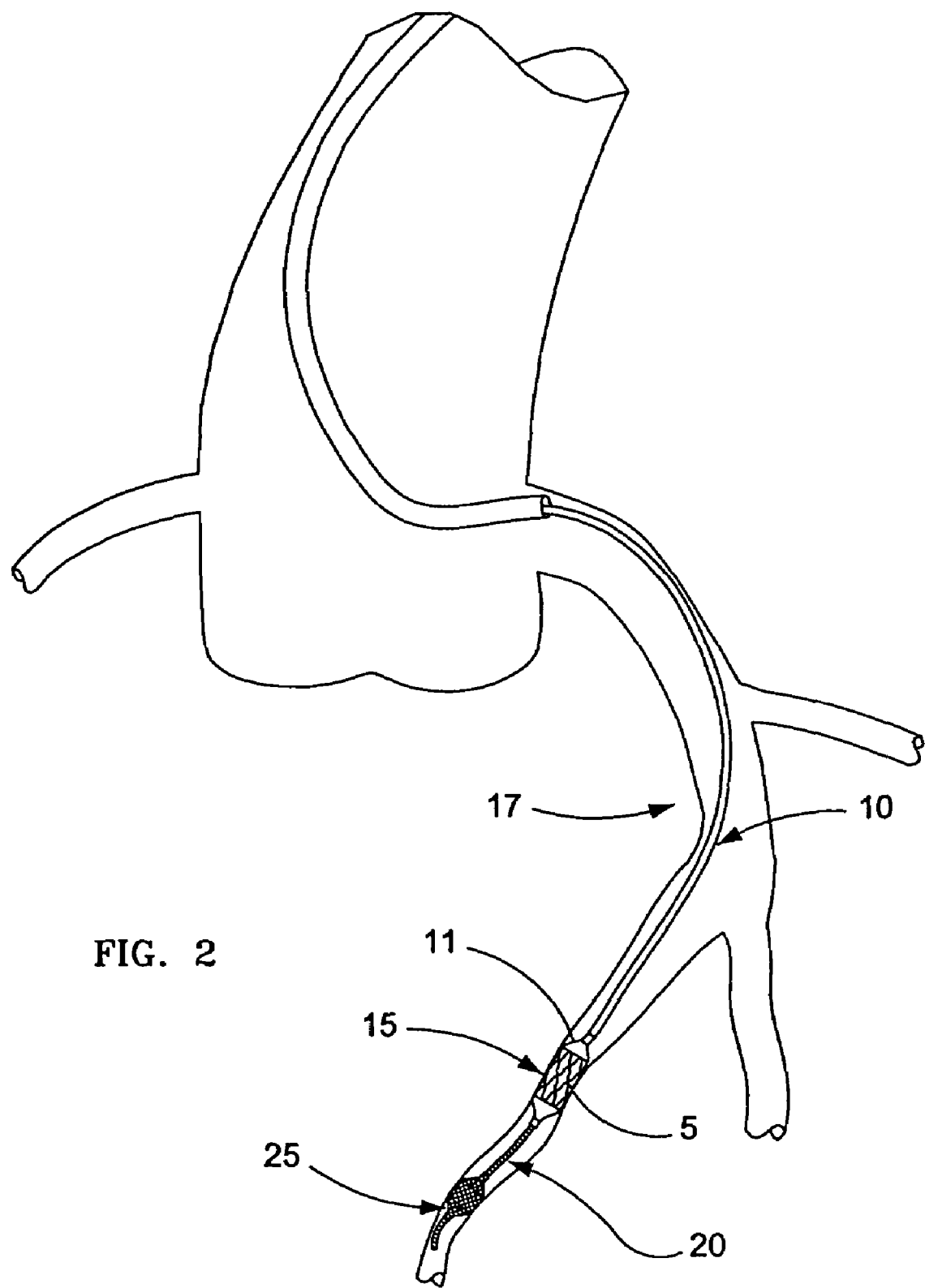
FIG. 2 is an illustration of a filter system in accordance with the invention deployed within a portion of the coronary arterial anatomy.

The present invention is a temporary filter guidewire for use in minimally invasive procedures, such as vascular interventions or other procedures where the practitioner desires to capture embolic material that may be dislodged during the procedure. Intravascular procedures such as PTCA or stent deployment are often preferable to more invasive surgical techniques in the treatment of vascular narrowings, called stenoses or lesions. With reference to FIG. 1 and FIG. 2, deployment of balloon expandable stent 5 is accomplished by threading catheter 10 through the vascular system of the patient until stent 5 is located within a stenosis at predetermined treatment site 15. Once positioned, balloon 11 of catheter 10 is inflated to expand stent 5 against the vascular wall to maintain the opening. Stent deployment can be performed following treatments such as angioplasty, or during initial balloon dilation of the treatment site, which is referred to as primary stenting.

Catheter 10 is typically guided to treatment site 15 by a guidewire. In cases where the target stenosis is located in tortuous vessels that are remote from the vascular access point, such as coronary arteries 17 shown in FIG. 2, a steerable guidewire is commonly used.

According to the present invention, filter guidewire generally designated as 20 guides catheter 10 to treatment site 15 and includes distally disposed filter 25 to collect embolic debris that may be generated during the procedure. The invention is directed to manipulating various types of temporary filters wherein relative movement of the filter ends either causes or accompanies transformation of the filter between a collapsed configuration and a deployed configuration. Such transformation may be impelled by external mechanical means or by self-shaping memory (either self-expanding or self-collapsing) within the filter. Preferably, filter 25 is self-expanding, meaning that filter 25 has a mechanical memory to return to the expanded, or deployed configuration. Such mechanical memory can be imparted to the metal comprising filter 25 by thermal treatment to achieve a spring temper in stainless steel, for example, or to set a shape memory in a susceptible metal alloy such as nitinol. Filter 25 preferably comprises a tube formed by braided filaments that define pores and have at least one inlet opening 66 that is substantially larger than the pores. Alternative types of filters may be used in filter 25, such as filter assemblies that include a porous mesh mounted to expandable struts.

Optionally, adding radiopaque markers (not shown) to filter ends 27, 29 can aid in fluoroscopic observation of filter 25 during manipulation thereof. Alternatively, to enhance visualization of braided filter 25 under fluoroscopy, at least one of the filaments may be a wire having enhanced radiopacity compared to conventional non-radiopaque wires suitable for braiding filter 25. At least the majority of braiding wires forming filter 25 should be capable of being heat set into the desired filter shape, and such wires should also have sufficient elastic properties to provide the desired self-expanding or self-collapsing features. Stainless steel, and preferably nitinol monofilaments are suitable for braiding filter 25. A braiding wire having enhanced radiopacity may be made of, or coated with, a radiopaque metal such as gold, platinum, tungsten, alloys thereof, or other biocompatible metals having a relatively high X-ray attenuation coefficient compared with stainless steel or nitinol. One or more filaments having enhanced radiopacity may be inter-woven with non-radiopaque wires, or all wires comprising filter 25 may have the same enhanced radiopacity.

Figure 21:
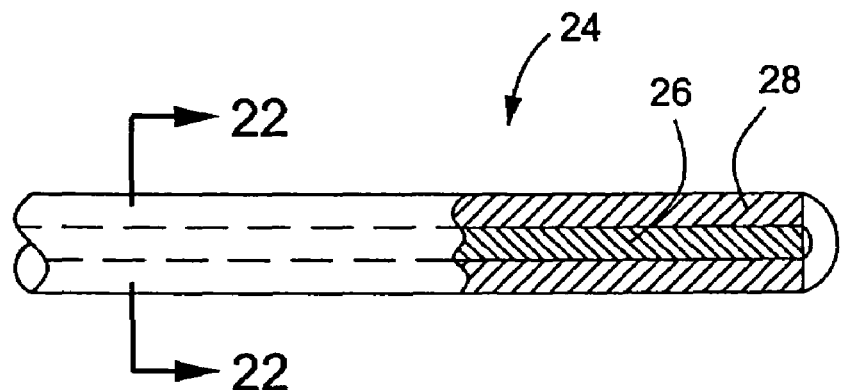
FIG. 21 is longitudinal partial section of a portion of enhanced radiopacity wire used in making a filter in accordance with the invention.
Figure 22:
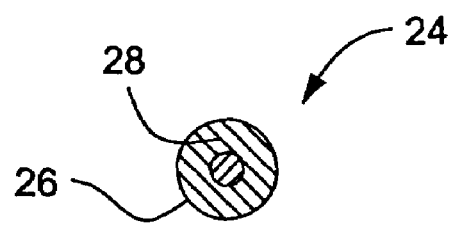
FIG. 22 is a transverse sectional view of enhanced radiopacity wire used in making a filter in accordance with the invention taken along the line 22-22 of FIG. 21.
Figure 23:
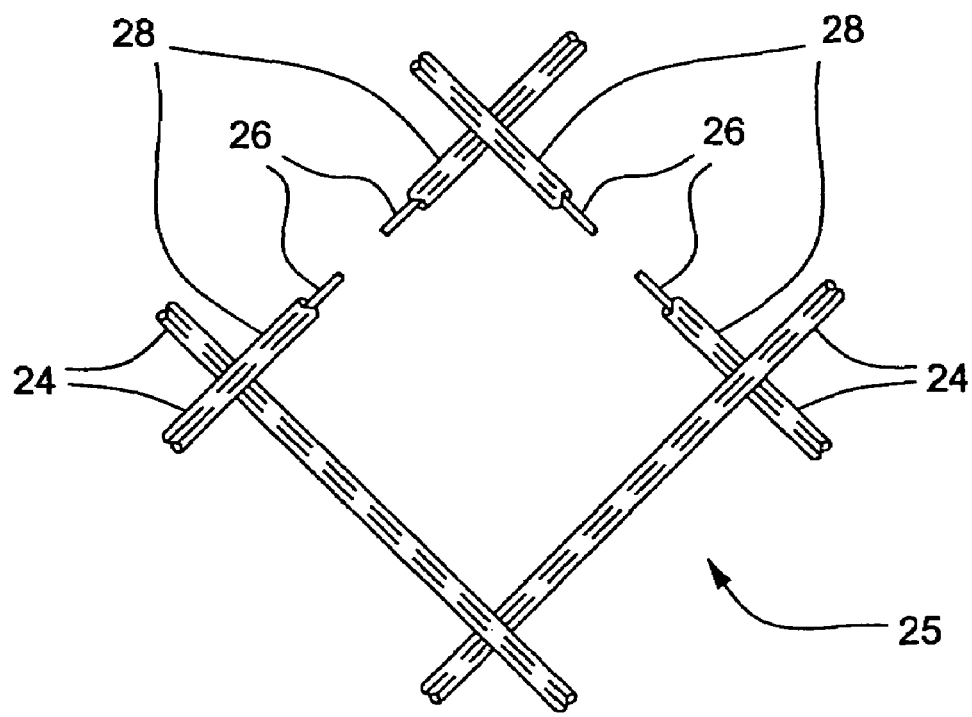
FIG. 23 is a portion of a braided filter in accordance with the invention, with portions of enhanced radiopacity braiding wire exposed.

Alternatively, as shown in FIGS. 21-23, one or more of the braid filaments may comprise composite wire 24, having radiopaque core 26 and non-radiopaque layer or casing 28. Such coaxial, composite wires are referred to as DFT (drawn-filled-tube) wires in the metallic arts, and are formed by inserting a solid billet of one metal into a hollow billet of a different metal, then repeatedly drawing and annealing the combination until a wire of desired diameter and hardness is achieved. A preferred DFT wire for use in the instant invention comprises a core of a 90% platinum-10% nickel alloy, and a casing of binary nickel-titanium (nitinol) alloy. By placing the more radiopaque, but more ductile material in the center of wire 24, the nitinol outer layer is able to provide the resulting wire with nearly undiminished mechanical properties. Conversely, placing a radiopaque coating or layer around a nitinol core substantially effects the physical properties of the wire. Thus, in comparison to nitinol monofilament wire, PtNi core/nitinol tube DFT wire has a greater X-ray attenuation coefficient and nearly identical mechanical properties. Wire 24, comprising a PtNi core/nitinol tube combination, provides improved radiopacity of filter 25 without giving up the shape-memory or pseudo-elastic properties of nitinol, which contribute to good shape-retention and the elastic transformation of filter 25 between collapsed and deployed configurations. In the preferred DFT combination of wire 24, core 26 makes up at least approximately 25% of the total cross-section of wire 24, by area. In making filter 25 in a size intended for use in vessels up to about 6 mm in diameter, wire 24 is preferably about 0.001-0.003 inch (0.03-0.08 mm) diameter, more preferably about 0.002 inch (0.05 mm) diameter. Such wires are available from Fort Wayne Metals Corp., Fort Wayne, Ind., U.S.A.

Figure 3:
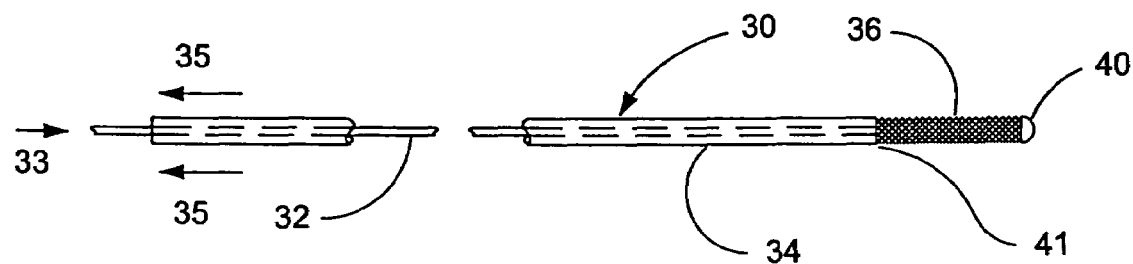
FIG. 3 is an illustration of a prior art expandable mesh device, shown with the mesh in a collapsed configuration.
Figure 4:
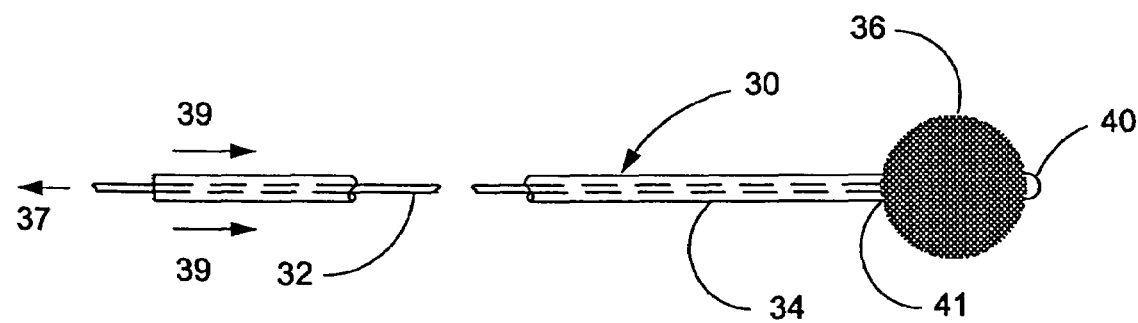
FIG. 4 is an illustration of a prior art expandable mesh device, shown with the mesh in a deployed configuration.

In accordance with the invention, maintaining filter 25 in a collapsed configuration during introduction and withdrawal of filter guidewire 20 does not require a control sheath that slidingly envelops filter 25. Thus, this type of device is sometimes termed Asheathless.@ Known types of sheathless vascular filter devices are operated by a Apush-pull@ mechanism that is also typical of other expandable braid devices, as shown in FIGS. 3 and 4. Prior art expandable braid device 30 includes core wire 32 and tubular shaft 34 slidably disposed thereabout. Tubular braid 36 surrounds core wire 32 and has a braid distal end fixed to core wire distal end 40 and a braid proximal end fixed to shaft distal end 41. To expand braid 36, core wire 32 is pulled and shaft 34 is pushed, as shown by arrows 37 and 39 respectively in FIG. 4. The relative displacement of core wire 32 and shaft 34 moves the ends of braid 36 towards each other, forcing the middle region of braid 36 to expand. To collapse braid 36, core wire 32 is pushed and shaft 34 is pulled, as shown by arrows 33 and 35 respectively in FIG. 3. This reverse manipulation draws the ends of braid 36 apart, pulling the middle region of braid 36 radially inward toward core wire 32.

Figure 5:
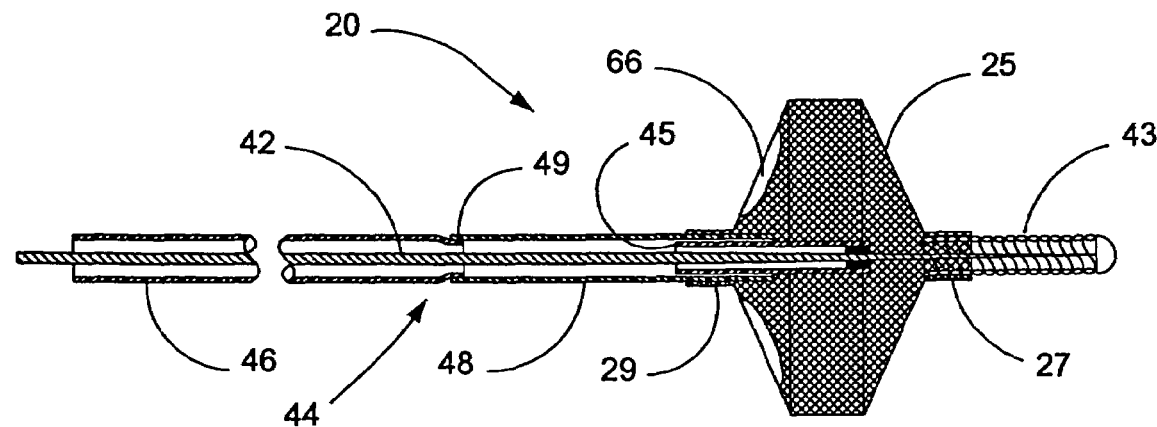
FIG. 5 is a longitudinal sectional view of a first guidewire filter embodiment in accordance with the invention.

Referring now to FIG. 5, in a first embodiment of the invention, filter guidewire 20 includes core wire 42 and flexible tubular tip member 43, which is preferably a coil spring, fixed around the distal end of core wire 42. Thin wires made from stainless steel and/or one of various alloys of platinum are commonly used to make such coil springs for use in guidewires. Core wire 42 can be made from shape memory metal, such as nitinol, or preferably is a stainless steel wire tapered at the distal end. For treating small caliber vessels such as coronary arteries, core wire 42 will preferably measure about 0.006 inch (0.15 mm) in diameter.

Tubular shaft 44 is slidably disposed around core wire 42, and includes relatively stiff proximal portion 46 and relatively flexible distal portion 48. Proximal portion 46 is preferably made from thin walled stainless steel tubing, usually referred to as hypotubing, although other metals can be used. Various metals or polymers can be used to make relatively flexible distal portion 48, although it is preferably made from thermoset polyimide tubing, available from sources such as HV Technologies, Inc., Trenton, Ga., U.S.A. The length of distal portion 48 may be selected as appropriate for the intended use of the filter guidewire. In one example, portion 48 may be designed and intended to be flexible enough to negotiate tortuous coronary arteries, in which case the length of portion 48 may be 15-35 cm (5.9-13.8 inches), preferably at least approximately 25 cm (9.8 inches). In comparison to treatment of coronary vessels, adaptations of the invention for treatment of renal arteries may require a relatively shorter flexible portion 48, and versions intended for approaching vessels in the head and neck may require a relatively longer flexible portion 48.

When filter guidewire 20 is designed for use in small vessels, shaft 44 may have an outer diameter of about 0.014 inch (0.36 mm). The general uniformity of the outer diameter is preferably maintained by connecting proximal portion 46 and distal portion 48 with lap joint 49. Lap joint 49 uses any suitable adhesive, preferably cyanoacrylate instant adhesives from Loctite Corporation, Rocky Hill, Conn., U.S.A., or Dymax Corporation, Torrington, Conn., U.S.A. Lap joint 49 can be formed by any conventional method such as reducing the wall thickness of proximal portion 46 in the region of joint 49, or by forming a step-down in diameter at this location with negligible change in wall thickness, as by swaging.

Expandable tubular filter 25 is positioned concentrically with core wire 42, and is sized such that when it is fully deployed, as shown in FIGS. 1 and 2, the outer perimeter of filter 25 will contact the inner surface of the vessel wall. The surface contact is preferably maintained around the entire vessel lumen to prevent any emboli from slipping past filter 25. Preferably, cyanoacrylate adhesive is used to secure filter distal end 27 to tip member 43, and to secure filter proximal end 29 near the distal end of shaft 44. Optionally, radiopaque marker bands (not shown), such as platinum rings, can be incorporated into the adhesive joints securing filter ends 27, 29 respectively to tip member 43 and shaft 44. Filter 25 is deployed by advancing, or pushing shaft 44 relative to core wire 42 such that filter distal and proximal ends 27, 29 are drawn toward each other, forcing the middle, or central section of filter 25 to expand radially. Filter 25 is collapsed by withdrawing, or pulling shaft 44 relative to core wire 42 such that filter distal and proximal ends 27, 29 are drawn apart from each other, forcing the middle, or central section of filter 25 to contract radially.

Transition sleeve 45 is fixed about core wire 42 and is slidably located within the distal end of flexible distal portion 48 of tubular shaft 44. Transition sleeve 45 is preferably made of polyimide tubing similar to that used in distal portion 48 and extends distally therefrom. By partially filling the annular space between core wire 42 and shaft 44, and by contributing additional stiffness over its length, sleeve 45 supports core wire 42 and provides a gradual transition in overall stiffness of filter guidewire 20 adjacent the distal end of shaft 44. Transition sleeve 45 is fixed to core wire 42, preferably with cyanoacrylate adhesive, such that relative displacement between shaft 44 and core wire 42 causes corresponding relative displacement between shaft 44 and sleeve 45. The length and mounting position of sleeve 45 are selected such that sleeve 45 spans the distal end of shaft 44 regardless of the configuration of filter 25 and the corresponding position of shaft 44 relative to core wire 42. When constructed as described above, filter guidewire 20 provides the functions of a temporary filter combined with the performance of a steerable guidewire.

Figure 6:
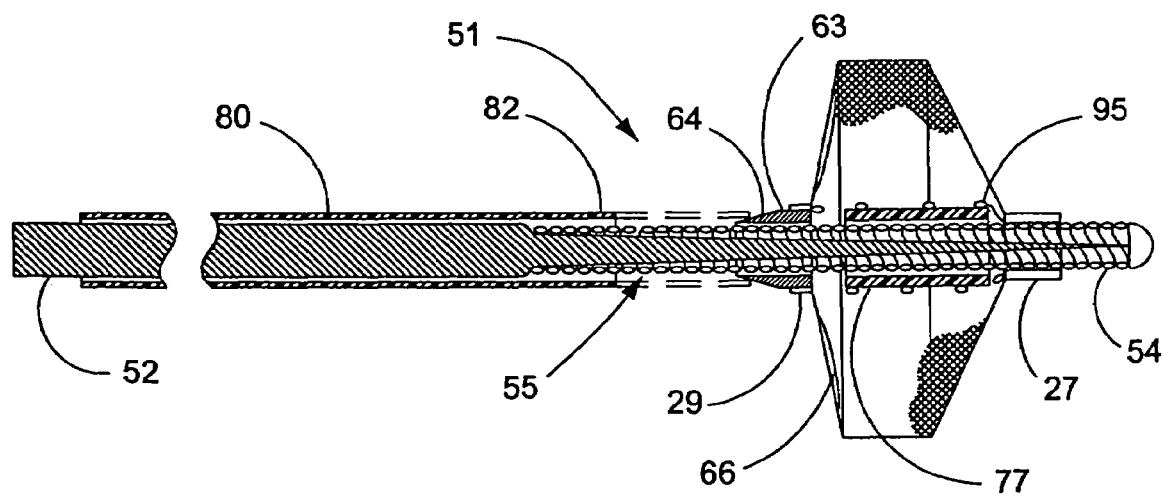
FIG. 6 is a longitudinal sectional view of a second guidewire filter embodiment in accordance with the invention.
Figure 7:
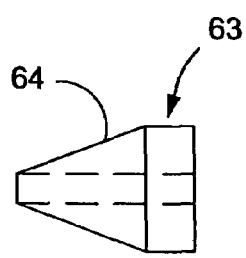
FIGS. 7-10 are illustrations of alternative actuators usable with the second guidewire filter embodiment in accordance with the invention.
Figure 8:
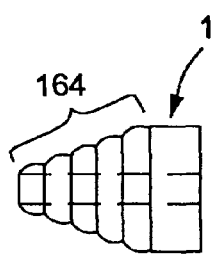
Figure 9:
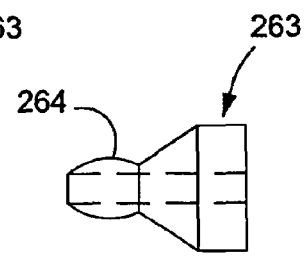
Figure 10:
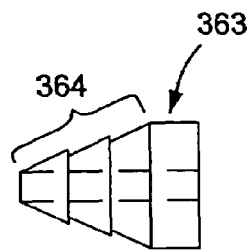

FIG. 6 depicts a second embodiment of the invention in which filter guidewire 51 incorporates a typical steerable guidewire 55 and deploys a self-expanding filter. Guidewire 55 comprises core wire 52, including a tapered distal end, and flexible tubular tip member 54, which is preferably a coiled spring, fixed there around. At least a distal portion of tip member 54 is preferably made from radiopaque metal wire, such as an alloy of platinum. Self-expanding filter 25 is mounted about guidewire 55, with filter distal and proximal ends 27, 29 being mounted slidably there along and, optionally, being fitted with radiopaque markers (not shown). Filter proximal end 29 is attached to actuator 63 using adhesive or solder. Actuator 63 is mounted slidably about guidewire 55 and is preferably made of shape memory metal, such as nitinol. Actuator 63 is illustrated in FIG. 7, with alternative actuators 163, 263 and 363 depicted in FIGS. 8, 9 and 10, respectively. In actuator 163, a series of ridges having increasing diameters presents tapered surface 164 for step-wise engagement with rod distal end 82. Actuator 263 provides a single ridge 264 for engagement with rod distal end 82. Rod distal end 82 can be formed with a complementary recess (not shown) to mate with ridge 264 for a snap-fit type engagement therewith. In actuator 363, a series of barbs having increasing diameters presents tapered surface 364 for step-wise engagement with rod distal end 82. A variety of other designs for mating components can be applied to the invention to detachably join rod distal end 82 and actuator 63. Examples include male and female screw threads, hook and loop elements common in the field of textiles, or numerous mechanisms intended to temporarily join extension wires to guidewires, examples of which are shown in U.S. Pat. No. 4,827,941 (Taylor), U.S. Pat. No. 5,113,872 (Jahrmarkt et al.) and U.S. Pat. No. 5,133,364 (Palermo et al.).

Stop element 77 is preferably a polyimide tube or ring that is fixed about guidewire 55 at a location between filter distal end 27 and filter proximal end 29. This embodiment may include assist spring 95, which is preferably a coiled tension spring mounted around guidewire 55 inside filter 25, and having distal and proximal ends fixed to filter distal and proximal ends 27, 29, respectively. Spring 95 can assist in the deployment of filter 25 by providing tension between filter distal and proximal ends 27, 29. Spring 95 can be mounted around stop element 77, or spring 95 may have some turns of the coil attached directly to guidewire 55 such that spring 95 can replace stop element 77. Elongate hollow rod 80 is slidably and removably disposed along guidewire 55 such that rod distal end 82 is engageable with actuator 63, as shown in the alternate position in FIG. 6. Rod 80 can be made from metal such as stainless steel or nitinol, or preferably from a rigid polymer such as polyimide.

Figure 11:
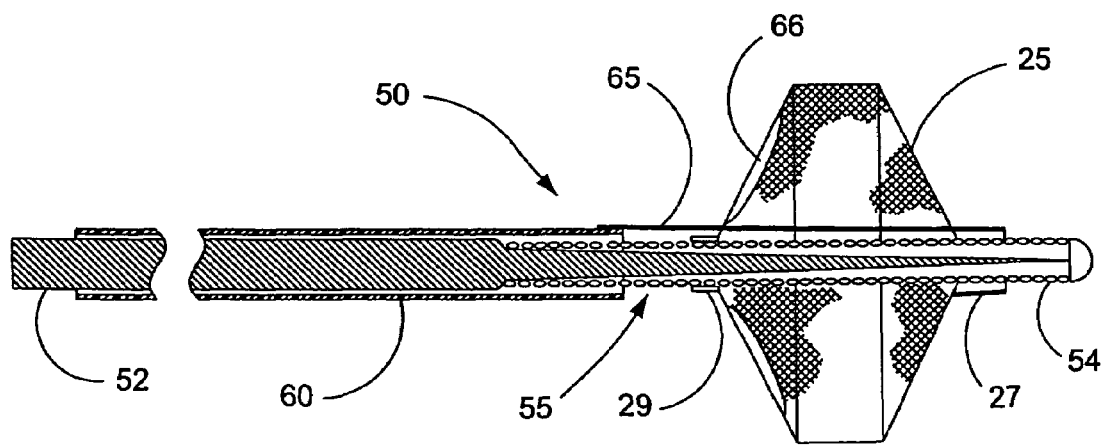
FIG. 11 is a longitudinal sectional view of a third guidewire filter embodiment in accordance with the invention.

FIG. 11 illustrates a third embodiment of the invention in which filter guidewire 50 also incorporates steerable guidewire 55, as described above with respect to filter guidewire 51. In filter guidewire 50, the mounting arrangement of filter 25 is reversed with respect to filter guidewire 20, such that filter distal end 27 is slidably mounted around and adjacent to the distal end of guidewire 55, and filter proximal end 29 is fixed to guidewire 55. Elongate tubular actuator 60 is slidingly and coaxially disposed around guidewire 55 proximal to filter 25. Link 65 movably extends through opening 66 in filter 25 adjacent filter proximal end 29 and connects the distal end of actuator 60 to filter distal end 27. Opening 66 is one of the inlet openings of filter 25, however any opening large enough to slidably pass link 65 will suffice. For example, a standard or over-sized pore in filter 25 may permit link 65 to extend therethrough. Actuator 60 can be made from thin walled metal tubing, such as stainless steel hypodermic tubing, or more preferably, polyimide tubing. When an embodiment of filter guidewire 50 is designed and intended for use in clinical applications with small-lumen catheters, such as PTCA catheters, then actuator 60 should have an outside diameter of 0.014 inch (0.36 mm) or less so that filter guidewire 50 can be slidably received within the guidewire lumen of the catheter. Link 65 is preferably a thin wire, such as stainless steel, measuring approximately 0.002 to 0.008 inch (0.05 to 0.20 mm) in diameter, most preferably 0.006 inch (0.15 mm). Alternatively, link 65 may be a non-metallic filament capable of pushing and/or pulling filter distal end 27.

Figure 14:
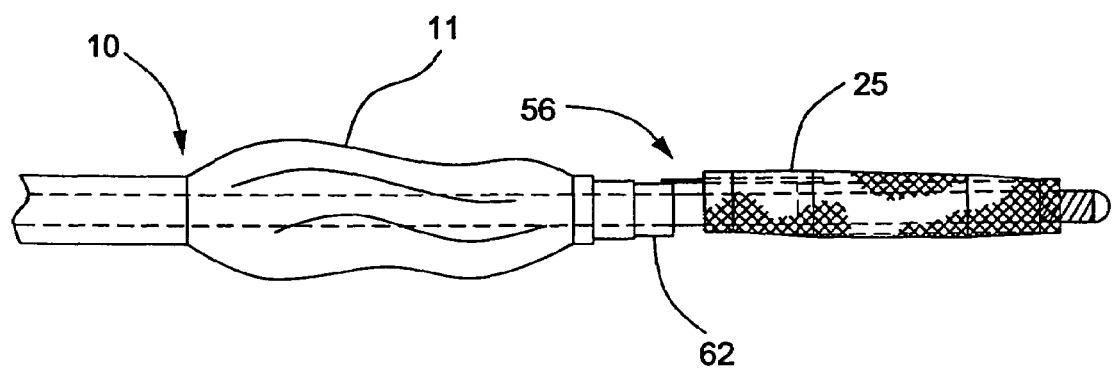
FIG. 14 is a longitudinal view of the fourth guidewire filter system embodiment in accordance with the invention, including a balloon catheter slidably positioned thereon, shown with the filter in a collapsed configuration.

Transformation of filter 25 from the deployed configuration to the collapsed configuration, shown in FIG. 14, is achieved by manipulating the proximal ends of guidewire 55 and actuator 60 as follows. Pushing actuator 60 distally while pulling guidewire 55 proximally causes link 65 to advance into filter 25 and displace filter distal end 27 distally along guidewire 55. The movement of filter distal end 27 away from filter proximal end 29, which is fixed to guidewire 55, forces filter 25 to collapse around guidewire 55 to a lower profile that is suitable for introduction to or withdrawal from the patient. The distal end of actuator 60 is spaced proximally from filter proximal end 29 a distance sufficient to permit a range of motion of actuator 60 without contacting filter proximal end 29. In this first version of the third embodiment of the invention, wherein filter 25 is self-expanding, link 65 is placed under compression loading to collapse filter 25, and thus link 65 is also referred to as a push rod.

Optionally, filter 25 may be self-collapsing, wherein its shape memory is to return to the collapsed configuration. In this second version of the third embodiment of the invention, deployment of filter 25 is achieved and maintained by pulling actuator 60 proximally while pushing guidewire 55 distally, which action draws filter distal end 27 and filter proximal end 29 towards each other and forces expansion of filter 25. In this embodiment, link 65 is placed under tension loading to deploy filter 25.

In the development of temporary guidewire filters, it has been determined that there may be practitioners who habitually tend to push the outer rod and pull the core wire when attempting to collapse the filter, which is contrary to the motion required in the conventional arrangements shown in FIGS. 3 and 4 and also in FIG. 5. Thus, the Areverse@ push-pull action required in the self-expanding version of filter guidewire 50 is a more natural motion for a number of users.

Figure 12:
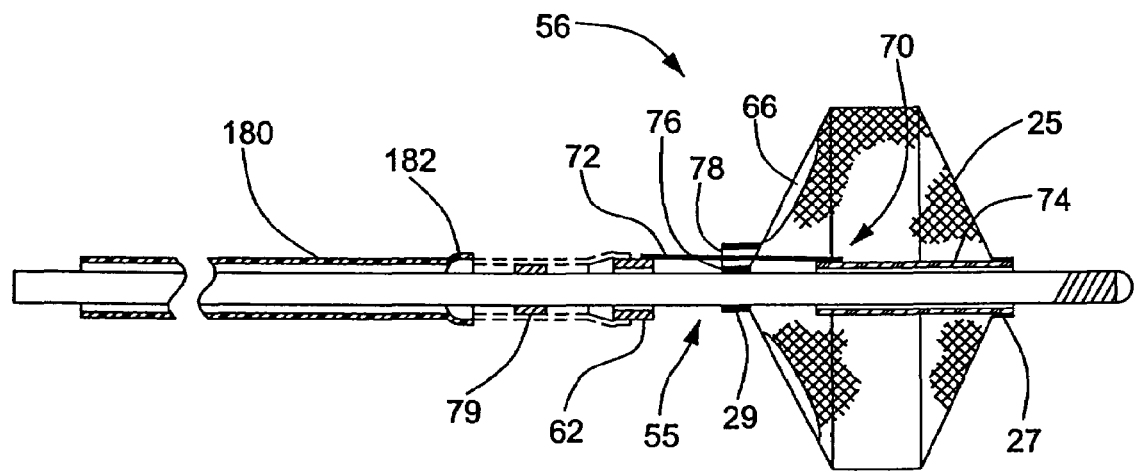
FIG. 12 is a longitudinal sectional view of a fourth guidewire filter embodiment in accordance with the invention, including a hollow rod slidably positioned thereon.

FIG. 12 depicts filter guidewire 56, which is a preferred fourth embodiment of the invention, and wherein self-expanding filter 25 is arranged over guidewire 55 similarly to filter guidewire 50, described above. In filter guidewire 56, actuator 62 is a short ring slidingly and coaxially disposed around guidewire 55 proximal to filter 25. Link 70 movably extends through opening 78 within filter proximal end 29 and connects actuator 62 to filter distal end 27. Link 70 includes link proximal segment 72 and link distal segment 74. Link distal segment 74 is a tubular element that is fixed to filter distal end 27 and is slidingly disposed around guidewire 55 within filter 25. Link distal segment 74 is made from thin walled tubing, preferably polyimide. Link proximal segment 72 is comparable to the wire of link 65, and extends from an attachment point on actuator 62 into filter 25 to connect with link distal segment 74. Joint 76 attaches filter proximal end 29 to guidewire 55, and includes opening 78, which guides link proximal segment 72 that is slidably disposed therethrough. Joint 76 may be made from any suitable fastening material such as adhesive, braze alloy, or preferably, solder. Preferably, opening 78 is formed by a short section of thin walled polyimide tubing (not shown), which is incorporated into joint 76 within filter proximal end 29. Alternatively, opening 78 can be formed by including a removable mandrel, such as a stainless steel wire coated with polytetrafluoroethylene (PTFE), in joint 76 during its formation. The fastening material of joint 76 will not adhere to the mandrel, which can be removed to leave opening 78.

Elongate hollow rod 180 is slidably and removably disposed along guidewire 55 such that rod distal end 182 is engageable with actuator 62. Rod distal end 182 is an over-sized section of rod 180 such that it will slidably fit over at least a proximal portion of actuator 62, as shown in the alternate position in FIG. 12. The engaged combination of rod 180 and actuator 62 can apply distally directed force to link 70, similarly to the operation of elongate actuator 60 in guidewire filter 50. Thus, pushing rod 180 distally while pulling guidewire 55 proximally causes link 70 to advance into filter 25 and translate filter distal end 27 along guidewire 55 in a distal direction. The movement of filter distal end 27 away from filter proximal end 29, which is fixed to guidewire 55, forces filter 25 to collapse around guidewire 55 to a lower profile for introduction to or withdrawal from the patient. Actuator 62 is spaced proximally from filter proximal end 29 a distance sufficient to permit a range of motion of actuator 62 without contacting filter proximal end 29. Optionally, rod distal end 182 can be an unexpanded end of rod 180, similar to rod distal end 82 of rod 80, in which case rod distal end 182 may simply abut actuator 62 without extending thereover.

Optional stop 79, preferably a ring, may be fixed to guidewire 55 proximal to actuator 62. Stop 79 can prevent interventional catheters positioned on guidewire 55 from engaging and moving actuator 62 and unintentionally collapsing filter 25. Stop 79 is smaller in diameter than actuator 62 such that rod 180 may be sized to slide over stop 79 and engage actuator 62, as shown in the alternate position in FIG. 12.

There are advantages to filter guidewire 56, besides the more habitual Areverse@ push-pull action that it shares with filter guidewire 50, described above. In filter guidewire 50, guidewire 55 must be small enough to fit slidably inside of actuator 60 which, in turn, must fit inside the guidewire lumen of a therapeutic catheter. In filter guidewire 56, guidewire 55 can be large enough to fill the guidewire lumen of the same sized therapeutic catheter, because elongate rod 180 can be removed and replaced with the catheter. Thus, a larger, more standard sized guidewire can be included in the filter device, with the attendant performance advantages that accompany such an increase in size.

Figure 13:
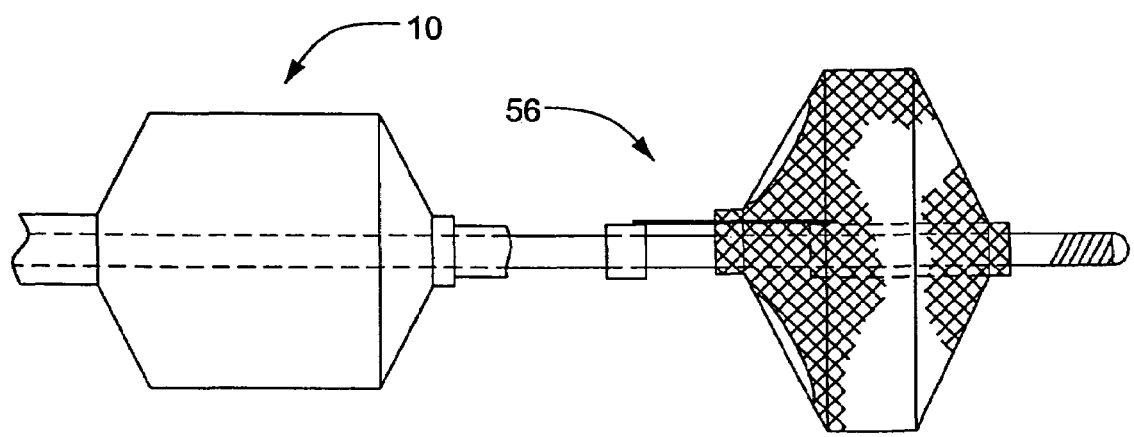
FIG. 13 is a longitudinal view of the fourth guidewire filter system embodiment in accordance with the invention, including a balloon catheter slidably positioned thereon, shown with the filter in a deployed configuration.

As an alternative to the arrangements shown in FIGS. 6 and 12, it may be desirable to use a catheter, such as catheter 10, to operate actuators 63, 62 of guidewire filters 51, 56 respectively, to collapse self-expanding filter 25. In such an arrangement, catheter 10 replaces rods 80, 180 in all respects, and no exchange is required therebetween. This simplified method of use can be performed during filter placement, during withdrawal, or both. FIG. 13 shows catheter 10 placed over filter guidewire 56, with optional stop 79 omitted therefrom. FIG. 14 shows the same arrangement as FIG. 13, with catheter 10 being advanced to operate actuator 62, causing filter 25 to collapse. As shown in FIG. 14, balloon 11 of catheter 10 would typically be deflated while catheter 10 is used to collapse filter 25.

Figure 15:
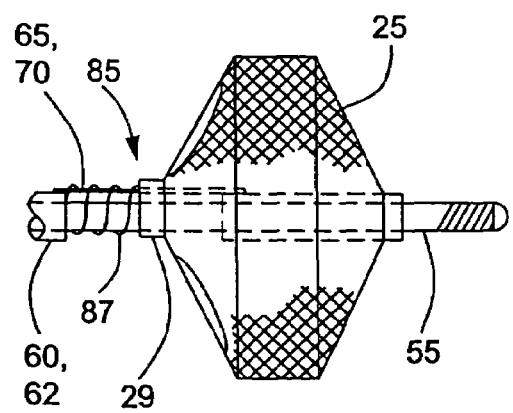
FIG. 15 is a side view taken of the distal portion of another guidewire filter system in accordance with the invention, showing a proximal assist spring.

FIG. 15 depicts filter guidewire 85, which is a modification of filter guidewires 50, 56, and is made by mounting proximal assist spring 87 around guidewire 55 between filter proximal end 29 and actuators 60, 62. In the preferred construction, a modification of filter guidewire 56, filter 25 is self-expanding, and spring 87 is a coiled compression spring that assists in the expansion of filter 25 by maintaining a separating force between filter proximal end 29 and actuator 62. Spring 87 can surround guidewire 55 only or, preferably, surround both guidewire 55 and link 65, 70, as shown. Alternatively, in a modification of filter guidewire 50, filter 25 is self-collapsing, with spring 87 being a coiled tension spring attached at its ends to filter proximal end 29 and actuator 60. To deploy such a self-collapsing version of filter 25, actuator 60 can apply proximally directed force to overcome the shape memory of filter 25 and the tension force in spring 87.

Figure 16:
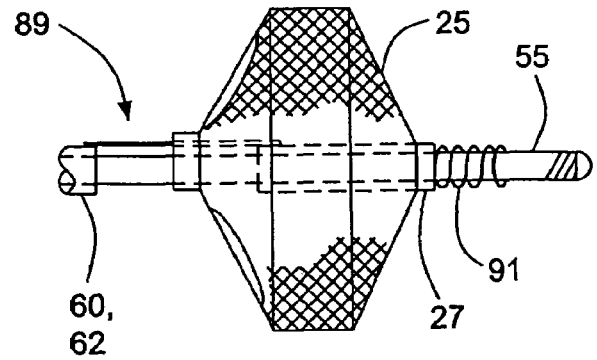
FIG. 16 is a side view taken of the distal portion of another guidewire filter system in accordance with the invention, showing a distal assist spring.

FIG. 16 depicts filter guidewire 89, which is another modification to filter guidewires 50, 56, and is made by mounting assist spring 91 around guidewire 55 distal to filter 25. In the modification of filter guidewire 56, filter 25 is self-expanding, with spring 91 being a coiled compression spring having a proximal end abutting filter distal end 27 and having a distal end fixed to guidewire 55. Spring 91 assists in the deployment of filter 25 by maintaining proximally directed force against filter distal end 27. Alternatively, in a modification of filter guidewire 50, filter 25 is self-collapsing, with spring 91 being a tension spring having a proximal end fixed to filter distal end 27 and having a distal end fixed to guidewire 55. To deploy such a self-collapsing version of filter 25, actuator 60 can apply proximally directed force to overcome the shape memory of filter 25 and the tension force in spring 91.

Figure 17:
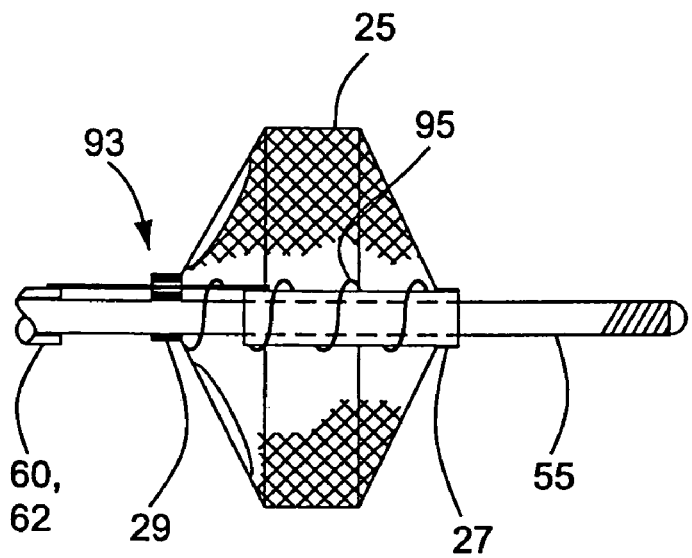
FIG. 17 is a partial longitudinal sectional view taken of the distal portion of another guidewire filter system in accordance with the invention, showing an assist spring inside the filter.

FIG. 17 depicts filter guidewire 93, which is another modification to filter guidewires 50, 56, and is made by mounting assist spring 95 around guidewire 55 and link distal segment 74 inside filter 25. In the modification of filter guidewire 56, filter 25 is self-expanding, with spring 95 being a coiled tension spring having a distal end attached to filter distal end 27 and having a proximal end attached to filter proximal end 29. Spring 95 assists in the deployment of filter 25 by maintaining tension between filter distal and proximal ends 27, 29. Alternatively, in a modification of filter guidewire 50, filter 25 is self-collapsing, with spring 95 being a coiled compression spring mounted between filter distal and proximal ends 27, 29. To deploy such a self-collapsing version of filter 25, actuator 60 can apply proximally directed force to overcome the shape memory of filter 25 and the compression force in spring 95. All of the above-mentioned coiled assist springs can be fabricated with fine metal wire of about 0.001 to 0.005 inch (0.03 to 0.13 mm) diameter, preferably nitinol wire having 0.003 inch (0.08 mm) diameter.

To adjust and maintain the relative longitudinal and/or rotational positions of guidewires and the surrounding tubular elements in the various embodiments of the invention, a removable handle device (not shown) of a type familiar to those of skill in the art may be used. Such handle devices can have telescoping shafts with collet-type clamps that grip respectively, core wire 42 and shaft 44 in filter guidewire 20, guidewire 55 and actuator 60 in filter guidewire 50, and guidewire 55 and rods 80, 180 in filter guidewires 51 and 56. The handle device can also serve as a steering handle, or Atorquer@ which is useful for rotating steerable-type guidewires that are incorporated in the instant invention.

Figure 18:
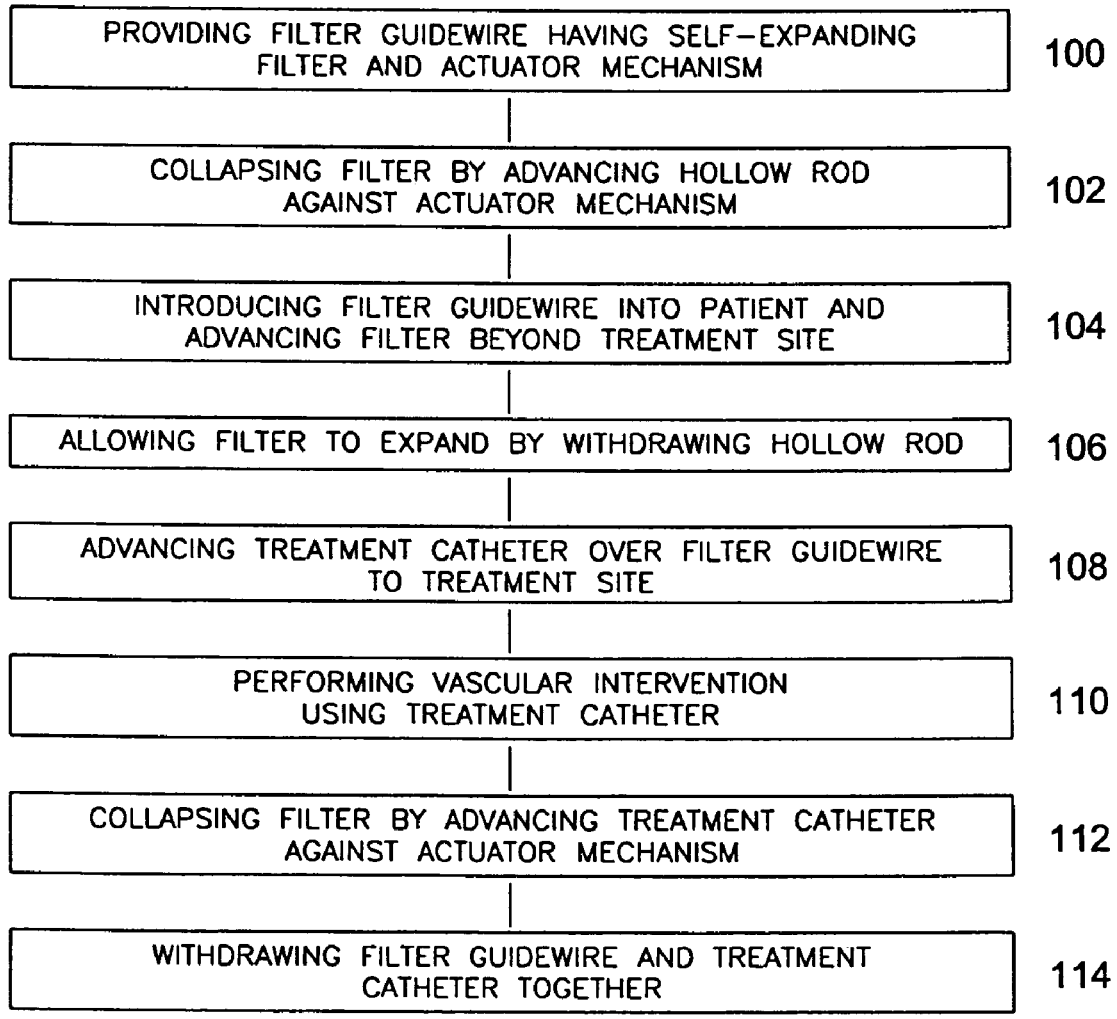
FIGS. 18 and 20 are flow charts depicting methods of using the guidewire filter system of the present invention.

The methods of using of the filter guidewires of the invention will be described below. Referring to FIG. 18, filter guidewire 85, having self-expanding filter 25 and actuator 62, is provided (step 100), and filter 25 is collapsed by advancing hollow rod 80 against actuator 62 (step 102). With filter 25 in the collapsed configuration, filter guidewire 85 is advanced into the patient=s vasculature until filter 25 is beyond the intended treatment site (step 104). Withdrawal of rod 80 allows filter 25 to expand under the combination of its own shape memory and the compression force of proximal spring 87 (step 106). With filter 25 deployed into contact with the vessel wall, a therapeutic catheter is advanced over filter guidewire 85 to the intended treatment site (step 108), and the therapy, such as balloon angioplasty, is performed (step 110). Any embolic debris generated during the therapy is captured in filter 25. After the therapy is completed, the therapeutic catheter is prepared for withdrawal, as by deflating the balloon, if so equipped, and the catheter is advanced against actuator 62 to cause filter 25 to collapse (step 112). Finally, while the catheter is used to continuously apply distally directed force against actuator 62 to maintain filter 25 in its collapsed configuration, filter guidewire 85 and the therapeutic catheter can be withdrawn together (step 114). Although the steps above describe using rod 80 and the therapeutic catheter to introduce and withdraw filter guidewire 56, respectively, it should be understood that variations are possible, since any tubular device that can engage and operate actuator 62 can be used, either during introduction or withdrawal.

Figure 20:
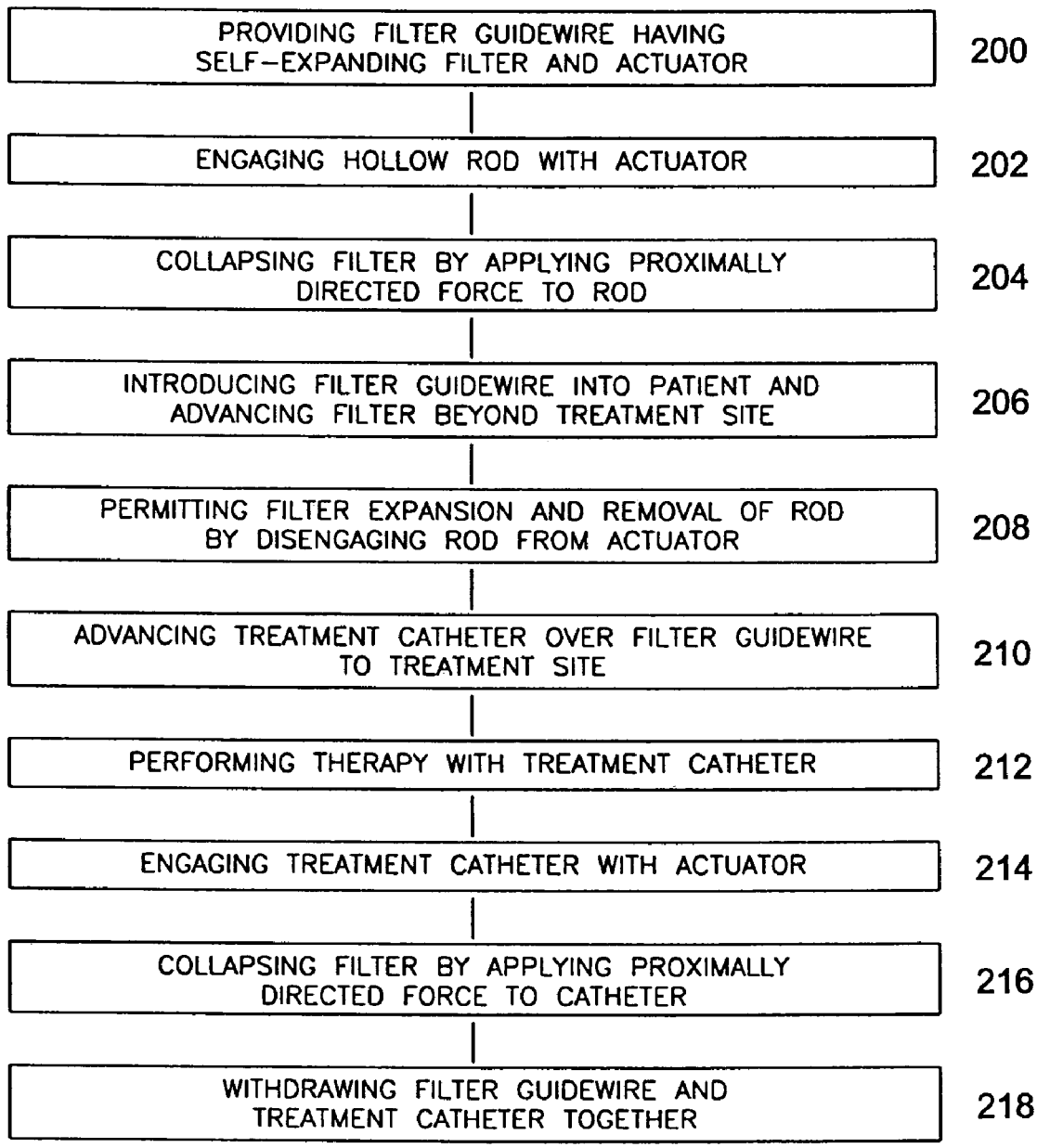

During use of filter guidewire 51, as shown in FIG. 20, rod 80 is first advanced over guidewire 55 until it engages actuator 63 (step 202). Pulling guidewire 55 proximally while pushing rod 80 distally against actuator 63 forces actuator 63 to slide distally until it is restrained by stop element 77. With actuator 63 thus restrained, rod 80 can attain a secure, albeit temporary, engagement with actuator 63 by wedging rod distal end 82 onto proximal taper 64 of actuator 63. To collapse filter 25, forces are applied to separate filter distal and proximal ends 27, 29. Proximally directed force is applied to filter proximal end 29 by pulling the engaged combination of rod 80 and actuator 63 proximally. Simultaneously, distally directed force is applied to filter distal end 27 by pushing guidewire 55 distally, which advances stop element 77 into contact with filter distal end 27. Applying a first degree of proximally directed force to rod 80 will cause filter 25 to collapse (step 204), such that filter guidewire 51 can be introduced into the patient and directed to the desired treatment site (step 206).

Once filter guidewire 51 has reached the intended location, applying a second, higher degree of proximally directed force to rod 80 will disengage rod 80 from actuator 63 (step 208). With rod 80 and actuator 63 thus disengaged, rod 80 can be withdrawn from the patient and filter 25 is free to expand under its mechanical memory, optionally assisted by spring 95. Once filter 25 has expanded to cover the lumen of the vessel distal to the treatment area, therapeutic catheter 10 is advanced over filter guidewire 51 (step 210) and the desired therapy is implemented (step 212). Upon completion of the treatment, catheter 10 is removed from filter guidewire 51 and is replaced with rod 80. Rod 80 is again engaged with actuator 63, as described above, to provide a first degree of proximally directed force for collapsing filter 25 and permitting withdrawal of filter guidewire 51 from the patient.

Figure 19:
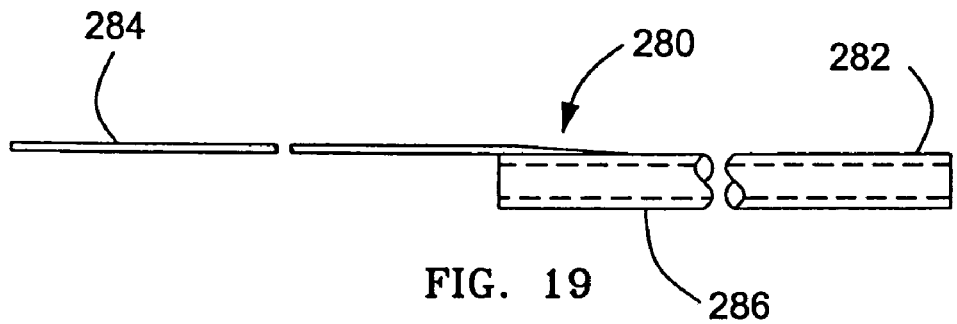
FIG. 19 is a side view of an alternative embodiment of a hollow rod for actuating guidewire filters in accordance with the second and fourth embodiments of the invention.

Filter guidewires 51, 56, as described above, utilize removable hollow rods 80, 180, respectively, to engage and manipulate actuators 63, 62, respectively. FIG. 19 depicts a rapidly exchangeable rod 280 for use with filter guidewires 51, 56. Rod 280 includes proximal shaft 284, and distal section 286, which is essentially a short portion of rods 80, 180. Distal section 286 is only about 10-30 cm (3.9-11.8 inches) long, making it easy to exchange over the portion of filter guidewire 51, 56 that extends outside of the patient, as is understood by those of skill in the field of intravascular catheters. Proximal shaft 284 preferably is a wire having a minimum diameter of about 0.012 inch (0.30 mm), and is tapered and attached to distal section 286. The stiffness of proximal shaft 284, and the secure attachment thereof to distal section 286 provide a rapidly exchangeable alternative to rods 80, 180 for pushing or pulling actions, as may be required. It will be understood that catheter 10 can also be of the rapid exchange type to facilitate interchanging rods and catheters.

While the invention has been particularly shown and described with reference to the preferred embodiments thereof, it will be understood by those skilled in the art that various changes in form and detail may be made therein without departing from the spirit and scope of the invention. For example, the invention may be used in any intravascular treatment utilizing a guidewire where the possibility of loosening emboli may occur. Although the description herein illustrates angioplasty and stent placement procedures as significant applications, it should be understood that the present invention is in no way limited to those environments.

What is claimed is:

1. A filter guidewire for capturing embolic material generated during treatment of a lesion in a vessel of a patient, the filter guidewire comprising:
    an elongate core wire having proximal and distal ends;
    an elongate tubular shaft slidably disposed along the core wire, the shaft including an elongate proximal portion and a short distal portion, the distal portion being more flexible than the proximal portion;
    a generally tubular filter mounted coaxially about the core wire, the filter having a distal end fixed to the core wire distal end and a proximal end fixed to the shaft distal portion, wherein relative displacement of the filter ends associated with longitudinal displacement between the tubular shaft and the core wire causes transformation of the filter between a collapsed configuration and a deployed configuration; and
    a transition sleeve fixed about the core wire distal end, the sleeve being slidably disposed within the shaft distal portion and extending distally there from.

2. The filter guidewire of claim 1 wherein the tubular shaft proximal portion comprises metal tubing.

3. The filter guidewire of claim 1 wherein the tubular shaft distal portion comprises polymeric tubing.

4. The filter guidewire of claim 1 wherein the transition sleeve comprises polymeric tubing.

5. The filter guidewire of claim 4 wherein the polymeric tubing comprises polyimide.

6. The filter guidewire of claim 3 wherein the polymeric tubing comprises polyimide.

7. The filter guidewire claim 1 wherein the transition sleeve is stiffer than the core wire distal end.

8. The filter guidewire of claim 1 further comprising a flexible tubular tip member fixed about the core wire distal end.

9. The filter guidewire of claim 8 wherein the tip member is disposed distally of the transition sleeve.

10. A filter guidewire comprising:
    an elongate core wire having proximal and distal ends;
    an elongate tubular shaft slidably disposed about the core wire, the shaft including an elongate proximal portion and a relatively short distal portion, the distal portion being more flexible than the proximal portion;
    a generally tubular filter mounted coaxially about the core wire, the filter having a filter distal end fixed to the core wire distal end and a filter proximal end fixed to the shaft distal portion; and
    a transition sleeve fixed about the core wire and spanning a distal end of the shaft to provide a gradual transition in overall stiffness of the filter guidewire adjacent the distal end of the shaft.

11. The filter guidewire of claim 10 wherein the transition sleeve partially fills an annular space between the core wire and the shaft.

12. The filter guidewire of claim 11 wherein the transition sleeve is slidably disposed within the shaft distal portion.

* * * * *